United States Patent [19]
Hoeft

[11] Patent Number: 5,494,031
[45] Date of Patent: Feb. 27, 1996

[54] APPARATUS AND METHOD FOR MEASURING CARDIAC OUTPUT

[76] Inventor: Andreas Hoeft, 2521 Wordsworth Ave., Houston, Tex. 77030

[21] Appl. No.: 203,674

[22] Filed: Feb. 28, 1994

Related U.S. Application Data

[63] Continuation of Ser. No. 855,307, Mar. 23, 1992, abandoned.

[30] Foreign Application Priority Data

Mar. 25, 1991 [DE] Germany .......................... 41 09 720.3

[51] Int. Cl.$^6$ ........................................................ A61B 5/00
[52] U.S. Cl. ........................... 128/633; 128/665; 128/713
[58] Field of Search ........................... 128/633, 664–666, 128/691–694, 713; 364/413.03

[56] References Cited

U.S. PATENT DOCUMENTS

| | | | |
|---|---|---|---|
| 4,167,331 | 9/1979 | Nielsen | 128/633 |
| 4,417,588 | 11/1983 | Houghton et al. | 128/713 |
| 4,874,949 | 10/1989 | Harris et al. | 128/664 |
| 5,054,916 | 10/1991 | Kanda et al. | 128/633 |
| 5,158,082 | 10/1992 | Jones | 128/633 |

OTHER PUBLICATIONS

Basset et al, "Simultaneous Detection of Deuterium Oxide and Indocyanine Green in Flowing Blood", *Journal of the American Physiology Society*, 1981, pp. 1367–1371.

*Primary Examiner*—Lee S. Cohen
*Assistant Examiner*—Robert L. Nasser, Jr.
*Attorney, Agent, or Firm*—Willian Brinks Hofer Gilson & Lione

[57] ABSTRACT

An apparatus and method for measuring cardiac output in a patient, The sensed pulsatile component of light at at least two wavelengths transmitted through or reflected from a site on the patient is measured. The measurements are used to calculate the relative concentration of an indicator dye relative to a reference dye, the concentration of the latter being known. Calibrated absolute concentration time curves are then calculated for the indicator dye.

3 Claims, 2 Drawing Sheets

APPARATUS AND METHOD FOR MEASURING CARDIAC OUTPUT

This application is a continuation of application Ser. No. 07/855,307, filed Mar. 23, 1992 now abandoned.

FIELD OF THE INVENTION

This invention relates generally to the measurement of cardiac output. It relates particularly to the measurement of cardiac output by non-invasive analysis of indicator dye curves.

BACKGROUND OF THE INVENTION

Cardiac output is a very important parameter for evaluation of total cardiac performance in a patient. Measurement of this parameter is a valuable tool in clinical practice as well as in research. Measurements are normally performed on critically ill patients or during major heart surgery. In patients who require pharmacologic support with potent vasoactive drugs, measurement of cardiac output is considered to be necessary.

It is well known to measure cardiac output in patients using an indicator dilution technique. In this technique, a known amount of dye, or a known amount of a cold liquid in the form of a cold saline bolus, for example, is injected into the patient's circulation. This is preferably done into the right atrium. An indicator dilution curve is then measured downstream in the pulmonary artery or the aorta.

Using this technique, cardiac output can be calculated from the area under the indicator dilution curve and the amount of the indicator. The indicator dilution curve is a dye concentration curve or a temperature curve, depending upon whether a dye or a cold liquid was injected. However, this method for measuring cardiac output requires assessment of indicator curves by invasive measurement through a catheter in the pulmonary artery or aorta. Because the use of invasive catheters is associated with significant risk, measurement of cardiac output in this manner is confined to critically ill patients in which the risk-benefit ratio is considered to be reasonable.

There have been attempts to measure an indicator dilution curve using an indocyanine green dye non-invasively. However, these attempts differ significantly from the present invention. Essentially, the previous attempts have tried to quantify an absolute concentration of intravascular indocyanine green dye concentration by direct measurement of light transmission or reflection. However, this did not produce accurate results because the Lambert-Beer law is not valid for light transmitted through tissues because multiple light scattering occurs. In these attempts the pulsatile nature of the lights signal was a handicap to the measurement and was generally filtered out.

SUMMARY OF THE INVENTION

An object of the present invention is to provide a new and improved apparatus and method for non-invasively measuring cardiac output.

It is another object of the invention to provide an apparatus and method for non-invasively measuring cardiac output by the assessment of an indicator concentration time curve.

The foregoing objects and others are realized in accord with the present invention by measuring light transmitted through or reflected from a patient's finger, for example. In contrast to previous attempts, the measurements are used to calculate the relative concentration of an indicator dye relative to a reference dye. A convenient reference dye for intravascular indicator dye concentration measurements is hemoglobin, which is physiologically already part of the blood, although other artificial reference dyes can be added to the blood and used. In the invention, the absolute concentration of the reference dye is determined from a blood sample, in-vitro. With hemoglobin, for example, its concentration is a laboratory parameter which is normally measured in all patients. Knowing the absolute concentration of the reference dye, calibrated absolute concentration time curves can be calculated for an indicator dye.

According to the invention, measurements are performed at at least two wavelengths on the pulsatile components of the signals. The reference dye and the indicator dye are chosen so as to have different absorption properties at these two wavelengths. In order to obtain a good, signal-to-noise ratio, one of these wavelengths should be in a range of maximum light absorption for the indicator dye. The second wavelength should be in a range where the light absorption for the indicator dye is at a minimum, but where the reference dye still has significant absorption.

The selection of wavelengths can be made by using monochromatic or narrow band width light sources. In the alternative, a light source with a wide spectrum can be used and the selection of wavelength made with optical filters at the light detector. Also, both methods can be combined in order to enhance signal-to-noise ratio.

In a practical application of the invention, hemoglobin is used as a reference dye and indocyanine green is used as an indicator dye. Indocyanine green has a maximum absorption at 800 nm and virtually no absorption above 900 nm. Thus, the desired wavelengths for non-invasive indocyanine green measurement are one at 800 nm and a second wavelength in the infrared range above 900 nm. Preliminary studies with these two wavelengths produced good results.

Regarding the results, dye curves which are measured at a peripheral site on the body, e.g., on a finger, might show a slow onset and a relatively flat shape for the indicator dilution curve due to low perfusion at the measuring site. In such case, it is sometimes difficult to eliminate recirculating dye from the first pass of the dye bolus. One solution to this problem is enhancement of perfusion at the measurement site by using warming devices or local vasodilating agents.

In the alternative, where low perfusion at the measuring cite results in these indicator dilution curve characteristics, the problem can be solved when the time course of the recirculating dye contribution to the indicator dilution curve is known. In order to obtain sufficient information on the characteristics of recirculation of the indicator dye, a longer time period for data collection is used. This time period must be sufficiently long to include the early distribution phase of the indicator dye as well as the beginning of the elimination phase. The process of recirculation can be described by an enhanced mathematical analysis of the total dye dilution curve. By using the additional information on a recirculation process, the configuration of an accurate first pass for a dye dilution curve can be extracted for calculation of cardiac output.

BRIEF DESCRIPTION OF THE DRAWINGS

The foregoing and other objects of the invention are illustrated more or less diagrammatically in the drawings, in which.

DESCRIPTION OF THE PREFERRED EMBODIMENT

Figure 1:
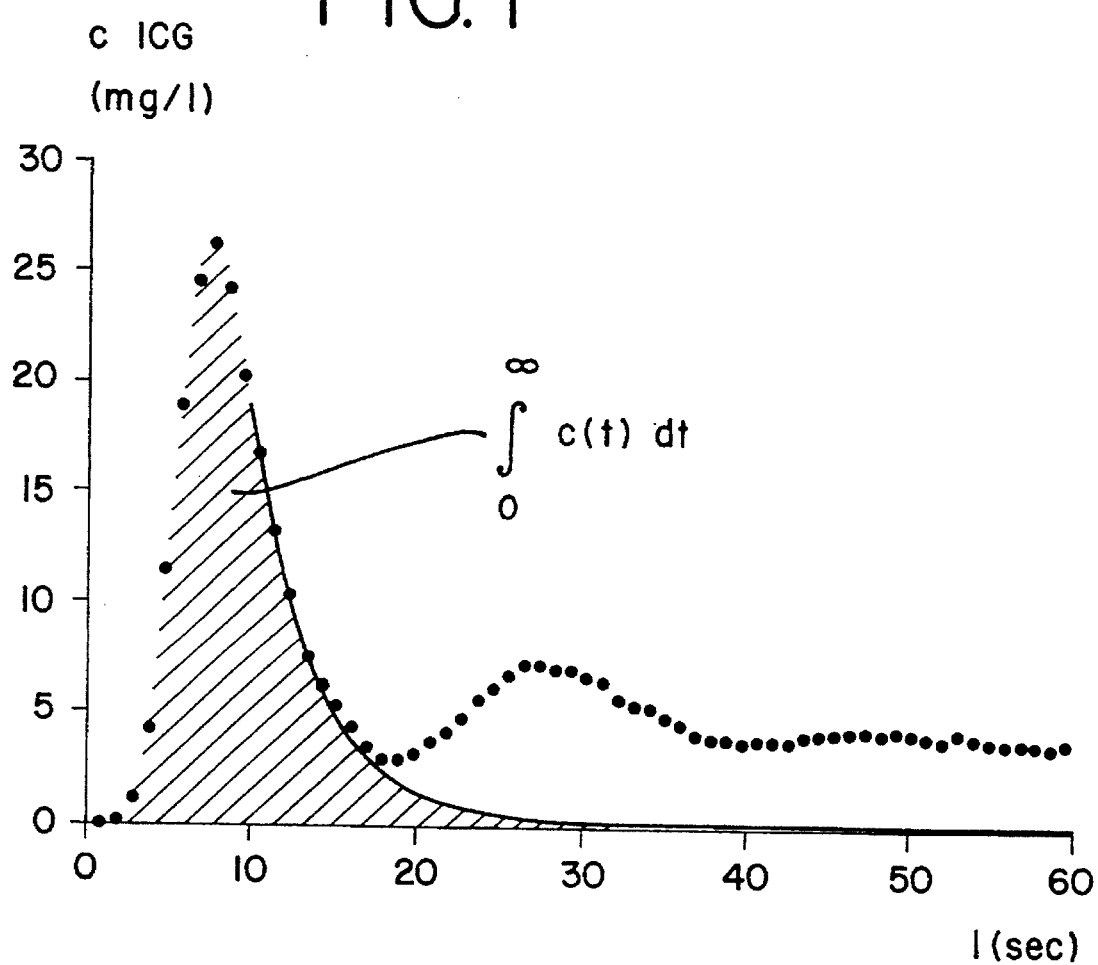
FIG. 1 is a typical concentration time course for an indicator dye after injection of the dye bolus.

Referring now to the drawings, and particularly to FIG. 1, a typical concentration time course of an indicator dye is illustrated. In the example illustrated, 25 mg of indocyanine green were injected into the right atrium and the resulting concentration time course was measured in the aorta. In this regard, it must be noted that the present invention is not completely non-invasive in that the indicator dye must be placed in the bloodstream. However, patients normally are receiving fluids intravenously during this type of a treatment and the dye bolus can readily be injected in this way.

As seen in FIG. 1, the first peak is followed by a second peak which is due to recirculation of the dye. Cardiac output is determined by calculation of the area under the curve of the first peak. A monoexponential extrapolation is performed on the downslope of the curve of the first peak in order to eliminate recirculation as an effect. The hatched area depicts the area under the first peak curve, which is used for calculation of cardiac output. Cardiac output, which is measured by the hatched area under the curve, can then be calculated using the well-known Stewart Hamilton calculation:

$$CO = M_0 / \int c_{ind}(t) \, dt$$

Theoretically, a curve similar to that shown in FIG. 1 results from measurement at any site on the patient. However, the more peripheral the site of measurement is, the more delayed is the onset of the curve and the smaller the amplitude of the curve. Where, in addition, there is low profusion, it is frequently difficult to identify the first peak and to perform a monoexponential extrapolation on the downslope of the first peak. Once again, improvement of perfusion at the site of the measurement can counteract this effect or, in the alternative, an enhanced mathematical analysis made in the manner hereinbefore discussed.

Figure 2:
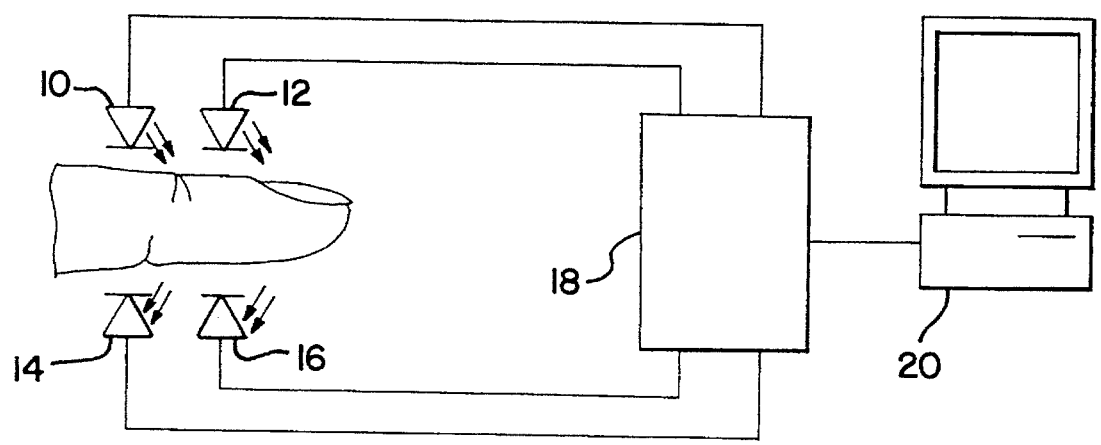
FIG. 2 is a schematic diagram of the measurement apparatus of the invention.

Referring now to FIG. 2, a schematic diagram of the apparatus for non-invasive measurement of dye concentration curves according to the invention is illustrated. In this apparatus, two light sources 10 and 12 and two light detectors 14 and 16 are utilized. They are part of an analog circuit 18 connected to a digital computer 20 through an analog-to-digital converter. The apparatus, including its light sources, detectors, analog circuitry and computer may be of the type now used in a pulse oximeter, for example.

Where indocyanine green is used as an indicator dye for measurement of .cardiac output, the light source 10 emits light at 800 nm and the light source 12 emits light above 900 nm. For example, the light emission wavelength for the light source 10 might be 940 nm.

The light detectors 14 and 16 are designed to be preferentially sensitive to the respective wavelengths. In the alternative, as has been pointed out, a single detector which is sensitive to both wavelengths may be used, alternately, to receive light emissions from both sources 10 and 12. Appropriate sites for non-invasive measurement are the patient's finger, earlobe, nose, face or forehead.

In operation of the apparatus, the light signals $I_{ind}(t)$ and $I_{ref}(t)$ are received by the light detectors 14 and 16, respectively. In a manner similar to the processing in a pulse oximeter, these signals are processed by the analog circuit 18 and then digitized, after which they are processed by the computer 20.

In a first normalization step, normalized pulsatile components of the light intensities ($I_{indpulse}(t)$ and $I_{refpulse}(t)$) are extracted from the raw signals for each wavelength by dividing pulsatile component by non-pulsatile component. In a second step, a signal which is a function of the pulsatile components is then derived as $M(t)=f_1(I_{indpulse}(t), I_{refpulse}(t))$. The ratio of indicator dye concentration to reference dye concentration ($C_{ind/ref}(t)$) can be related to M(t) based on a monoton calibration function:

$$C_{ind/ref}(t) = f_{cal}(M(t))$$

The absolute concentration of the dye ($c_{ind}(t)$) can then be calculated based on the known concentration of the reference dye ($c_{ref}$), e.g., hemoglobin as follows:

$$C_{ref} = \text{constant} = C_{hemoglobin},$$

$$C_{ind}(t) = f_{ref}(C_{ind/ref}(t), C_{hemoglobin})$$

Figure 3:
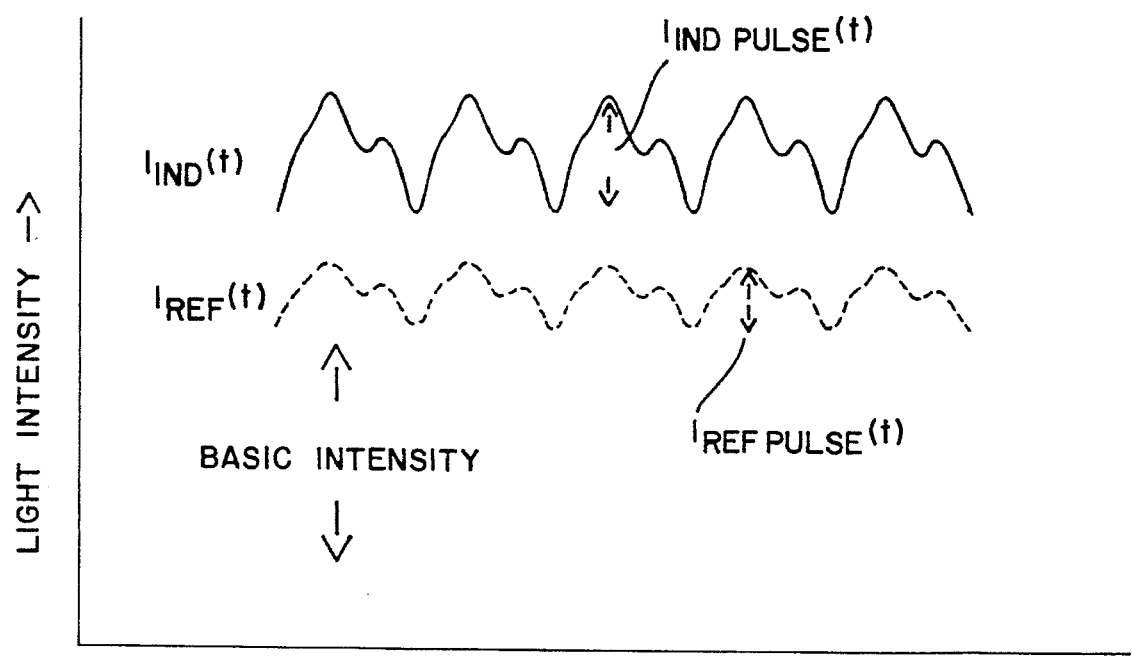
FIG. 3 is a graphic representation of the time course of the light intensities which are measured with the apparatus shown in FIG. 2.

Referring now to FIG. 3, a schematic representation of the light intensities as measured by the light detectors is shown. A nonvarying or basic light intensity level is determined primarily by the absorption and scattering of light in the tissues and in the nonpulsatile venous compartment. The pulse varying portion of the light intensities are mainly determined by the absorption and scattering properties of compartments which contain pulsatile blood flow in the patient, i.e., arteries and arterial capillaries.

The pulsatile components of both wavelengths are constant if no indicator dye is present in the circulation, e.g., if no indocyanine green and only hemoglobin is present. After the indicator dye injection, the pulsatile component in the range of maximum absorption of the indicator dye ($I_{indpulse}(t)$) will change in a more pronounced manner than that of the referenced wavelength ($I_{refpulse}(t)$), where absorption of the indicator dye is minimal. A relation of $I_{indpulse}(t)$ to $I_{refpulse}(t)$ is a function of the relation of the arterial intravascular indicator dye concentration to the reference dye concentration.

The invention has been described in the context of using hemoglobin as an intravascular reference dye. It is presently considered preferable because it is commonly measured in routine patient care and it is reasonable to assume that its concentration during measurement is constant. However, theoretically it is also possible to use another reference dye which is injected before the indicator dye solution is put into circulation. However, the concentration time course of the referenced dye must also be known if it is not constant.

The invention has also been described in the context of using two light transmission wavelengths. However, three or more wavelengths can also be used. Whereas the two wavelengths technique assumes constancy of oxygen saturation throughout the measurement, oxygen saturation can be simultaneously determined if three wavelengths are used.

While a preferred embodiment of the invention has been described, it should be understood that the invention is not limited to it. Modifications may be made without departing from the invention. The scope of the invention is defined by the appended claims, and all devices and methods that come within the meaning of the claims, either literally or by equivalents, are intended to be embraced therein.

I claim:

1. A method of measuring cardiac output in a body's circulation, comprising the steps of:
   a) injecting a defined amount ($M_o$) of an indicator dye into the body's circulation to establish an indicator dye concentration time course therein, said dye concentration time course having a distribution phase and an elimination phase;
   b) directing light non-invasively into the body at a chosen site;
   c) non-invasively detecting light transmitted through or reflected from the body at two wavelengths and determining its intensity;
   d) measuring the indicator dye concentration from the detected light intensity;
   e) determining the concentration time course ($c_{ind}(t)$) of the indicator dye;
   f) utilizing a reference dye having a known concentration in the circulation to determine the concentration time course of the indicator dye relative to the reference dye;
   g) measuring the concentration time course of the indicator dye over a period which permits the indicator dye distribution phase and elimination phase to be assessed by mathematical modeling of the measured concentration time course;
   h) using additional information regarding recirculation and elimination of the indicator dye to calculate cardiac output from dye curves with slow onset and slow downslope due to low perfusion at the site; and
   i) calculating the cardiac output from the amount of indicator dye injected ($M_o$) and from the indicator dye concentration time course ($c_{ind}(t)$) using the formula $$CO = M_o / \int c_{ind}(t)\, dt.$$

2. A method of measuring cardiac output in the circulation of a human body, comprising the steps of:
   a) injecting a defined amount ($M_o$) of an indicator dye into the body's circulation to establish an indicator dye concentration time course therein;
   b) directing light non-invasively into the body at a chosen site;
   c) non-invasively detecting light transmitted through or reflected from the body at two wavelengths and determining its intensity;
   d) measuring the indicator dye concentration from the detected light intensity;
   e) utilizing a reference dye having a known concentration in the circulation to determine the concentration time course of the indicator dye relative to the reference dye;
   f) using the pulsatile components of the light intensities ($I_{ind\,pulse}(t)$ and $I_{ref\,pulse}(t)$) to compute a derived parameter ($M(t)$, where $M(t)=f_m(I_{ind\,pulse}(t), I_{ref\,pulse}(t))$ with $f_m$ being the ratio of $I_{ind\,pulse}(t)$ and $I_{ref\,pulse}(t)$, $M(t)$ being related to the ratio of the indicator dye to the reference dye ($c_{ind/ref}(t)$) by a calibration function ($c_{ind/ref}(t)=f_{cal}(M(t))$;
   g) deriving an absolute concentration time course ($c_{ind}(t)$) of the indicator dye required for the calculation of cardiac output from ($c_{ind/ref}(t)$) and a known intravascular concentration of the reference dye ($c_{ref}$) ($c_{ind}(t)=f_{ref}(c_{ind/ref}(t), c_{ref})$; and
   h) calculating the cardiac output from the amount of indicator dye injected ($M_o$) and from the absolute indicator dye concentration time course ($c_{ind}(t)$) using the formula $$CO = M_o / \int c_{ind}(t)\, dt.$$

3. A method of measuring cardiac output in a body's circulation comprising the steps of:
   a) injecting a defined amount ($M_o$) of an indicator dye into the body's circulation to establish an indicator dye concentration time course therein;
   b) directing light non-invasively into the body at a chosen site;
   c) non-invasively detecting light transmitted through or reflected from the body at two wavelengths and determining its intensity;
   d) determining the indicator dye concentration from the detected light intensity;
   e) using pulsatile components of the light intensities at the two wavelengths to compute a derived parameter ($M(t)$, $M(t)$ being related to the amount of indicator dye by a calibration function;
   f) using (t) deriving an absolute concentration time course ($c_{ind}(t)$ of the indicator dye required for the calculation of cardiac output; and
   g) calculating the cardiac output from the amount of indicator dye injected ($M_o$) and from the absolute indicator dye concentration time course ($c_{ind}(t)$) using the formula $$CO = M_o / \int c_{ind}(t)\, dt.$$

* * * * *

UNITED STATES PATENT AND TRADEMARK OFFICE
CERTIFICATE OF CORRECTION

PATENT NO. : 5,494,031
DATED : February 27, 1996
INVENTOR(S) : Andreas Hoeft

It is certified that error appears in the above-identified patent and that said Letters Patent is hereby corrected as shown below:

On the title page, under item [56] under line 1, please insert a new line: --4,407,290  10/1983  Wilber ..... 128/633--.

In column 2, line 2, under "ABSTRACT" replace "," with --;--.

In the Claims

Claim 2, line 1, replace "the" with --a body's--.

Claim 2, line 2, delete " of a human body".

Claim 2, line 23, immediately after "($C_{ind}(t)$" insert --)--.

Claim 2, line 25-26, delete "intravascular".

Claim 3, line 17, delete "(t)" and replace with --M(t)--.

Signed and Sealed this

Twenty-second Day of June, 1999

Attest:

Q. TODD DICKINSON

Attesting Officer      Acting Commissioner of Patents and Trademarks